United States Patent
Gonopolskiy et al.

(10) Patent No.: US 7,741,592 B1
(45) Date of Patent: Jun. 22, 2010

(54) PHYSIOLOGICAL SENSOR WITH BOOSTER CIRCUIT

(75) Inventors: Oleg Gonopolskiy, West Bloomfield, MI (US); Arik Anderson, Birmingham, MI (US); Bruce J. Barrett, Birmingham, MI (US); Ronald A. Widman, Macomb, MI (US)

(73) Assignee: Somanetics Corporation, Troy, MI (US)

( * ) Notice: Subject to any disclaimer, the term of this patent is extended or adjusted under 35 U.S.C. 154(b) by 0 days.

(21) Appl. No.: 12/330,840

(22) Filed: Dec. 9, 2008

(51) Int. Cl.
*H03F 3/08* (2006.01)

(52) U.S. Cl. .................. 250/214 A; 250/214.1; 250/214 R; 600/340; 600/323

(58) Field of Classification Search ............. 250/214.1, 250/214 R, 214 A; 600/340, 323
See application file for complete search history.

(56) References Cited

U.S. PATENT DOCUMENTS

| 5,902,235 A | 5/1999 | Lewis et al. |
| 6,615,065 B1 | 9/2003 | Barrett et al. |
| 2002/0027704 A1* | 3/2002 | Kobayashi et al. ....... 359/341.1 |

* cited by examiner

*Primary Examiner*—Seung C Sohn
(74) *Attorney, Agent, or Firm*—Radar, Fishman & Grauer PLLC

(57) ABSTRACT

A physiological sensor includes a light source in optical communication with a light detector. A controller is in communication with the light detector via a connector. A booster circuit is in communication with the light detector and the connector. The booster circuit may be configured to buffer signals generated by the light detector and reduce an input capacitance on either the controller or terminals of the connector. In various embodiments, the booster circuit may be disposed on the connector for a reusable cable or a disposable sensor pad.

22 Claims, 3 Drawing Sheets

US 7,741,592 B1

PHYSIOLOGICAL SENSOR WITH BOOSTER CIRCUIT

BACKGROUND

Physiological sensors are used in medical applications to help doctors diagnose, monitor, and treat patients. The sensors use spectroscopy to provide valuable information about the body tissue. Spectroscopy generally refers to the dispersion of light as it travels through a medium. Light in some regions of the electromagnetic spectrum may disperse differently than light in other regions of the electromagnetic spectrum. For instance, light in the near-infrared region of the electromagnetic spectrum may disperse differently when traveling through body tissues than light in other regions.

A physiological sensor employing near-infrared spectroscopy may be used to detect characteristics of various body tissues by transmitting and receiving near-infrared light through the body tissue, and outputting a signal to a controller that provides valuable information about the body tissue. The information may be used by a doctor to diagnose, monitor, or treat the patient. In some instances, it is necessary to irradiate a single body tissue with different wavelengths of light, and to detect the light at multiple locations. Therefore, multiple sensors are placed in multiple locations, and the sensors are configured to sequentially operate, which requires a long sampling time. However, if too much light is absorbed or dispersed, or if the sampling time is not long enough, the near-infrared light will either not be received or the signal will be too weak to be reliable. Furthermore, a cable connecting a light detector to a controller may cause additional signal losses.

Previous attempts to correct for the weak signal include providing an amplifier with a feedback resistor that minimizes noise created by the amplifier. However, making the value of the feedback resistor too high could severely degrade the performance of the amplifier. In addition, the input impedance of the amplifier may have the characteristics of an inductor. Thus, the light detector and cable capacitance in combination with the amplifier result in a resonant circuit (such as an inductor-current tank) that oscillates. To dampen these oscillations, a capacitor is usually connected in parallel with the feedback resistor and, additionally, the capacitor reduces the bandwidth of the amplifier.

Accordingly, a physiological sensor is needed that provides more accurate and reliable data when too much light is absorbed or dispersed by the medium, or when the sampling time is too short to be reliable. In addition, a physiological sensor is needed that prevents significant signal losses caused by cables that connect the light detector to the controller.

DETAILED DESCRIPTION

A physiological sensor is provided that compensates for weak signals transmitted from a light detector to a controller when too much light is absorbed or dispersed by a medium, such as body tissue, or when a sampling time is too small. The physiological sensor includes a light source that transmits light to the light detector through the medium. The controller is connected to the light detector via a connector. Signals transmitted from the light detector to the controller pass through a booster circuit configured to buffer the signal and reduce input capacitance on either the controller or the connector. In one embodiment, the booster circuit is disposed on the connector of a reusable cable. Alternatively, the booster circuit may be disposed on the connector of a disposable sensor pad. By buffering the signal, the booster circuit provides more reliable data to the controller, and allows longer cables to be used to connect the light detector and the controller. The controller may then output the signals to a display. When used in medical applications, a doctor may place a sensor pad housing the light source and light detector on or over a body tissue, and view the signals on the display to diagnose, monitor, and treat patients. The embodiments disclosed herein allow the booster circuit to be used with existing sensor pads, connectors, controllers, and cables. Accordingly, these embodiments reduce the cost of the sensor and provide backwards compatibility.

Figure 1:
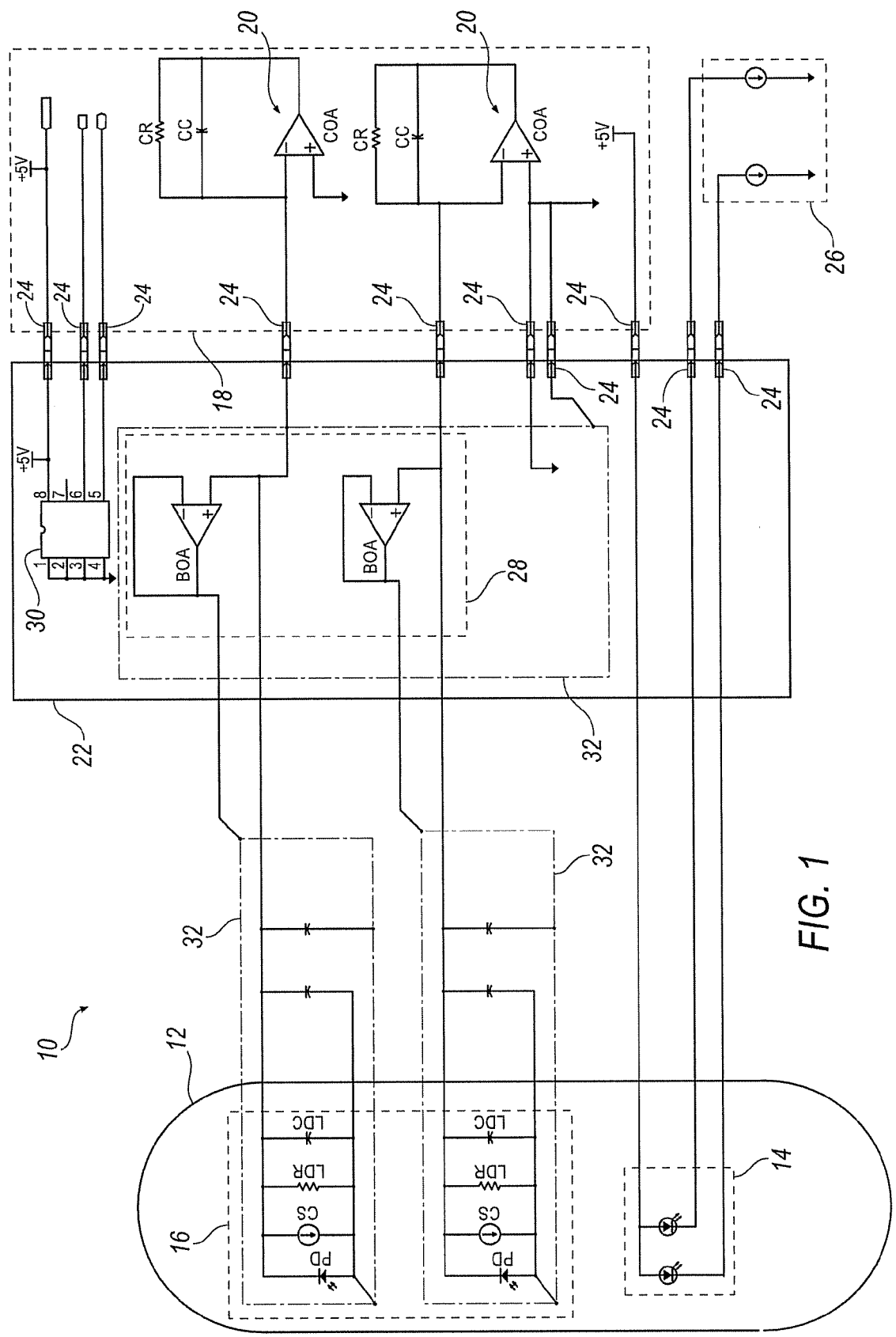
FIG. 1 is a diagram of the physiological sensor having a booster circuit disposed on a connector.

The Figures refer to exemplary embodiments wherein like numerals indicate like or corresponding parts throughout the several views. FIG. 1 illustrates an exemplary physiological sensor 10 having a sensor pad 12 that may be formed from a unitary article of manufacture. The physiological sensor 10 may further include a light source 14, such as a light emitting diode (LED) or any other type of light source 14 known. When the sensor pad 12 is placed on a medium, such as a body tissue, the light source 14 transmits light into the medium. The light source 14 may be configured to transmit light at a specific frequency or wavelength such as in a near-infrared region of the electromagnetic spectrum.

A light detector 16 is in optical communication with the light source 14 through the medium. The light detector 16 may include a photodiode or any other device capable of detecting light and communicating a signal when light is received. In one exemplary approach, the light detector 16 includes a photodiode PD, and a circuit model of the photodiode PD may include a diode, a current source CS, a resistor LDR, such as a parasitic shunt resistance, and a capacitor LDC, such as a junction capacitance. The light detector 16 may include additional or alternative components. For example, the exemplary physiological sensor 10 of FIG. 1 illustrates the light detector 16 having two photodiodes PD, two current sources CS, two resistors LDR, and two capacitors LDC. The light detector 16 may be configured to only communicate the signal when light in the near-infrared frequency region is received to reduce interference from other light sources. Moreover, if multiple light sources 14 are used, each light detector 16 may be configured to receive light from one or more of the light sources 14 based on, for example, the frequency of light transmitted by each light source 14. In addition, multiple light detectors 16 may be configured to receive light from a single light source 14.

Both the light source 14 and the light detector 16 may be disposed on the sensor pad 12, and the location of each the light detector 16 and light source 14 relative to one another may be dependent upon the medium. For instance, transmitting light through some mediums may require the light source 14 and the light detector 16 to be closer together or further apart. In an embodiment where the sensor pad 12 is formed from two or more articles of manufacture, some of the light sources 14 may be located on one sensor pad 12 while some of the light detectors 16 may be located on another sensor pad 12. Moreover, some of the light sources 14 and some of the light detectors 16 may be located on one sensor pad 12 while the remaining light sources 14 and light detectors 16 are located on another sensor pad 12.

The light detector 16 communicates signals to a controller 18 spaced from the sensor pad upon receiving light through the medium. The controller 18 may further include a processor and a memory device that stores executable code so that the controller 18 may process the signals received from the light detector 18. The controller 18 further includes a pre-amplifier 20, such as a trans-impedance amplifier, configured to convert a current signal from the light detector 16 into a voltage signal. In one approach, the trans-impedance amplifier includes an operational amplifier COA where the inverting input is in communication with the light detector 16 and the non-inverting input is grounded. In addition, a resistor CR and capacitor CC are in communication with the output and inverting input of the operational amplifier COA. The controller 18 may further include an output device such as a monitor (not shown) for displaying a graphical representation of the signal received from the light detector 16 so that a person, such as a doctor or other medical professional, using the sensor may view a representation of the signals communicated to the controller 18 from the light detector 16.

A connector 22 connects the light detector 16 to the controller 18. The connector 22 may be disposed on, and reduce the capacitance of, a reusable cable or a disposable sensor pad 12. Moreover, the connector 22 may be configured to connect existing sensor pads 12 and/or controllers 18 having predetermined pin configurations. This way, the connector 22 is backwards compatible and interchangeable with a plurality of different sensor pads 12 and controllers 18.

The connector 22 includes a plurality of connector terminals 24 that allow communication between the components on the sensor pad 12 and the controller 18. In addition, the connector may connect the components on the sensor pad 12 to other devices, such as a power supply 26. Each connector terminal 24 may have two plug ends to connect, for example, the light detector 16 to the controller 18. The connector terminal 24 may also be used to connect the light source 14 to the power supply 26. The total capacitance on the input of the controller 18 is the combined capacitance of a cable connecting the light detector 16 to the controller 18, and the light detector 16 itself. One way to reduce this capacitance is to reduce the length of the cable. Another way to reduce this capacitance is with a booster circuit 28. The booster circuit 28 may be disposed in the connector 22 regardless of the embodiment. For example, the booster circuit 28 may be disposed in the connector 22 of the disposable sensor pad 12, or alternatively, in the connector 22 of the reusable sensor cable. Accordingly, the booster circuit 28 reduces the capacitance of the disposable sensor pad 12 or the reusable sensor cable.

FIG. 1 is a diagram of one embodiment of the physiological sensor 10 having the booster circuit 28 configured to maintain a constant voltage across the light detector 16 and between electrodes of the light detector 16 and the cable to effectively reduce input capacitance. The location of the booster circuit 28 may affect how well the booster circuit 28 is able to buffer the signal communicated to the controller 18 and reduce the input capacitance. In the embodiment illustrated in FIG. 1, the booster circuit 28 is disposed on the connector 22 and is in communication with the light detector 16. In one exemplary approach, the booster circuit 28 may include an operational amplifier BOA where the inverting input is grounded and the non-inverting input is in communication with the light detector 16 and the controller 18 via the connector 22. In this exemplary approach, the booster circuit 28 acts as a voltage follower with a gain equal to 1 and is able to reduce capacitance of the cable. Other configurations of the booster circuit 28 may also be implemented. For example, in another exemplary approach, the booster circuit may include a trans-impedance amplifier in communication with the light detector 16 and the controller 18 to convert a current output by the light detector 16 into a voltage to be received by the controller 18. The trans-impedance amplifier may include the operational amplifier BOA where the inverting input is grounded, and the non-inverting input is in communication with the light detector 16 and the controller 18 via the connector 22. Other configurations of the booster circuit 28 may also be implemented, for instance, to remove the pre-amplifier 20. Each light detector 16 may be in communication with a dedicated booster circuit 28, as illustrated in FIG. 1.

The connector 22 includes a memory chip 30 configured to indicate whether the booster circuit 28 is present. Specifically, the memory chip 30 stores calibration data and communicates with the controller 18. Once the sensor pad 12 is connected to the controller 18 via the connector 22, the controller 18 reads the memory chip 30 and determines that the booster circuit 28 is present, and if so, the controller 18 supplies power to the booster circuit 28. The same approach may be used regardless of whether the connector 22 is disposed on the disposable sensor pad 12 or the reusable sensor cable. In these embodiments, the memory chip 30 may be connected to a communication bus (e.g., an inter-integrated circuit ($I^2C$) bus) and be in communication with another memory chip (not shown) disposed on the sensor pad 12. By connecting the memory chips to the same $I^2C$ bus, the connector 22 will not require additional pins.

In addition, a shield 32 may be used to prevent internal or external sources from interfering with the electrical components of the sensor 10. Specifically, one or more shields 32 may be placed around components of the light detector 16, such as the photodiodes PD. In addition, one or more shields 32 may be placed around the electrical components of the booster circuit 28, including the operational amplifiers BOA on the connector 22.

Figure 2:
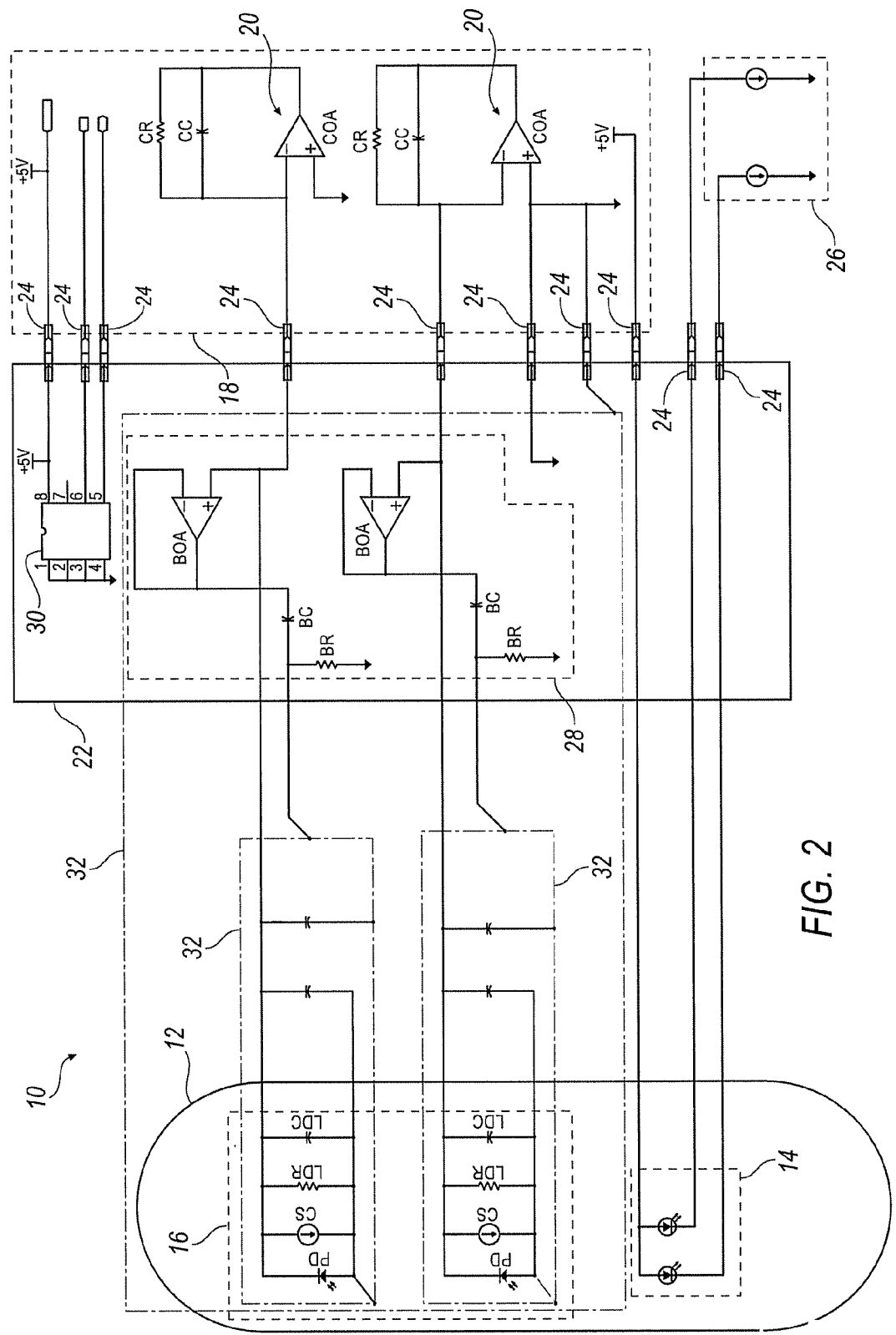
FIG. 2 is a diagram of the physiological sensor wherein the booster circuit includes an operational amplifier, a capacitor and a resistor.

FIG. 2 is a diagram of an embodiment of the physiological sensor 10 where the booster circuit 28 includes a capacitor BC. In this embodiment, the booster circuit 28 includes the trans-impedance amplifier previously discussed. In addition, the capacitor BC is electrically connected to the inverting input of the operational amplifier BOA and to a resistor BR that is grounded. As in the embodiment of FIG. 1, one or more shields 32 may be used to protect the components of the light detector 16 and/or the booster circuit 28 from interference.

Figure 3:
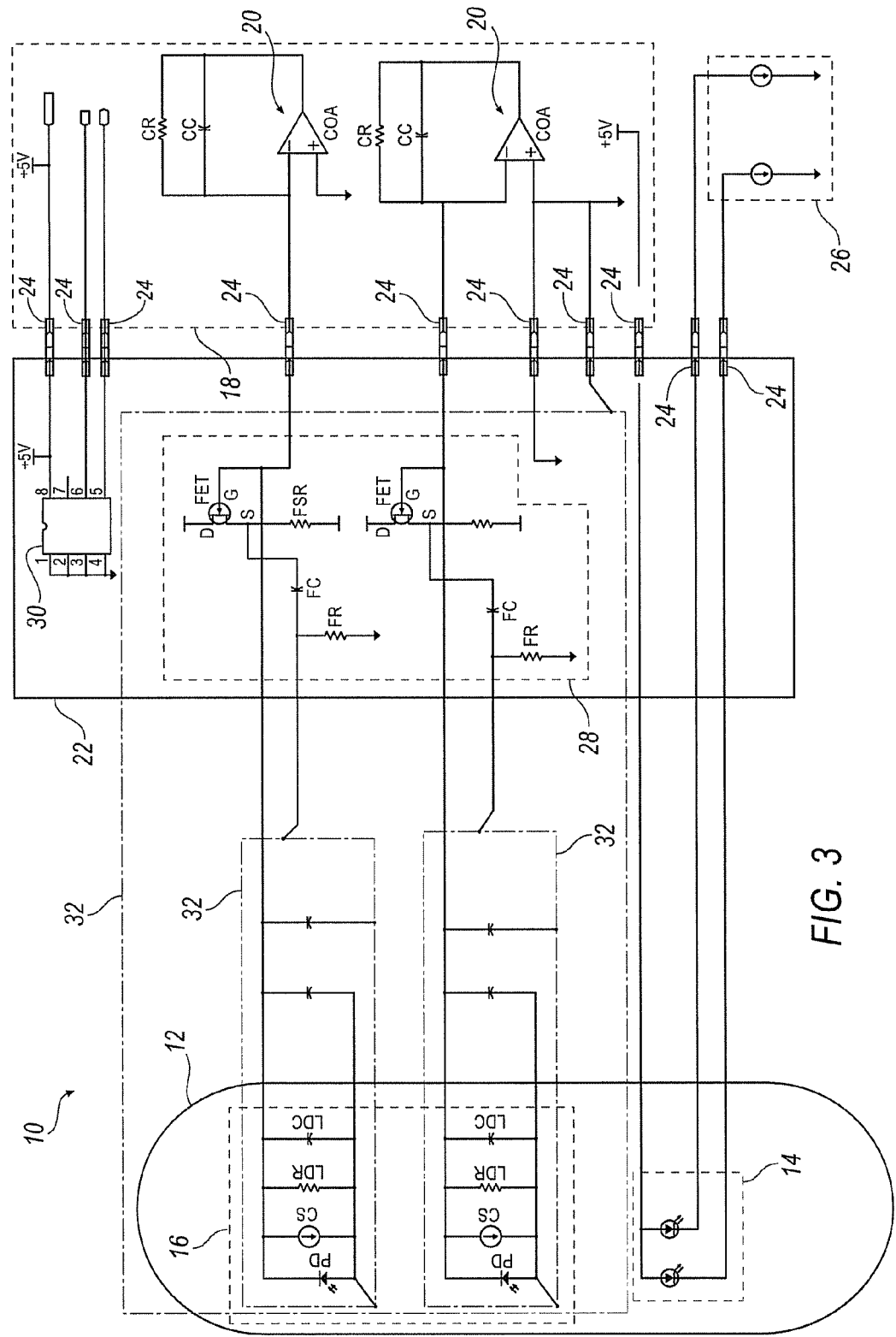
FIG. 3 is a diagram of the physiological sensor wherein the booster circuit includes a field effect transistor.

FIG. 3 is a diagram of an embodiment of the physiological sensor 10 where the booster circuit 28 includes a field effect transistor FET, such as a junction gate field effect transistor (JFET), instead of the trans-impedance amplifier to buffer the signal generated by the light detector 16. The booster circuit 28 may include an n-channel or p-channel JFET that includes a gate terminal G, a drain terminal D, and a source terminal S. An n-channel JFET is illustrated, and the gate terminal G is electrically connected to the inverting input of the trans-impedance amplifier of the controller 18 via the connector terminal 24, and the drain terminal D is connected to a voltage source. The source terminal S is electrically connected to a capacitor FC that is connected to a resistor FR that is grounded. Furthermore, the source terminal S is electrically connected to a grounded resistor FSR. As in the embodiments of FIGS. 1 and 2, one or more shields 32 may be used to protect the components of the light detector 16 and/or the booster circuit 28 from interference.

It is to be understood that the above description is intended to be illustrative and not restrictive. Many alternative approaches or applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. In sum, it should be understood that the invention is capable of modification and variation and is limited only by the following claims.

The present embodiments have been particularly shown and described, which are merely illustrative of the best modes. It should be understood by those skilled in the art that various alternatives to the embodiments described herein may be employed in practicing the claims without departing from the spirit and scope as defined in the following claims. It is intended that the following claims define the scope of the invention and that the method and apparatus within the scope of these claims and their equivalents be covered thereby. This description should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary.

What is claimed is:

1. A sensor comprising:
   a light source;
   a light detector in optical communication with said light source;
   a connector in communication with said light detector and said light source; and
   a booster circuit in communication with said light detector and wherein said booster circuit is disposed on said connector.

2. A sensor as set forth in claim 1, further comprising a sensor pad and wherein said light source and said light detector are disposed on said sensor pad.

3. A sensor as set forth in claim 2, wherein said sensor pad is formed from a unitary article of manufacture.

4. A sensor as set forth in claim 2, wherein said connector is spaced from said sensor pad.

5. A sensor as set forth in claim 1, wherein said connector includes plurality of terminals.

6. A sensor as set forth in claim 1, wherein each terminal is electrically connected to at least one of said light source and said light detector.

7. A sensor as set forth in claim 1, wherein said booster circuit includes at least one of a trans-impedance amplifier, an operational amplifier, a field effect transistor, and a capacitor.

8. A sensor as set forth in claim 1, wherein said connector is configured to communicate with a controller having an amplifier.

9. A sensor as set forth in claim 1, wherein said connector is disposed on a reusable cable.

10. A sensor as set forth in claim 1, wherein said booster circuit is configured to reduce an input capacitance on at least one of a controller in communication with said connector and said connector.

11. A sensor as set forth in claim 9, wherein said amplifier is a trans-impedance amplifier configured to convert current to voltage.

12. A sensor as set forth in claim 9, wherein said connector is interchangeable with a plurality of different sensor pads.

13. A sensor as set forth in claim 9, wherein said connector includes a memory chip configured to indicate the presence of said booster circuit.

14. A sensor as set forth in claim 13, wherein said memory chip is connected to a communication bus.

15. A sensor as set forth in claim 1, wherein said connector is disposed on a reusable sensor cable.

16. A sensor as set forth in claim 15, wherein said connector is interchangeable with a plurality of different sensor pads.

17. A sensor as set forth in claim 1, wherein said connector is backwards compatible.

18. A connector comprising:
   a plurality of terminals; and
   a booster circuit in communication with at least one of said plurality of terminals and wherein said booster circuit is configured to reduce an input capacitance of at least one of said plurality of terminals.

19. A connector as set forth in claim 18, wherein said booster circuit includes at least one of a trans-impedance amplifier, an operational amplifier, a field effect transistor, and a capacitor.

20. A connector as set forth in claim 18, further comprising a memory chip configured to indicate the presence of said booster circuit.

21. A connector as set forth in claim 18, wherein said memory chip is connected to a communication bus disposed on a sensor pad.

22. A sensor comprising:
   a sensor pad having a light source and a light detector circuit in optical communication with said light source, said sensor pad being configured to be disposed on body tissue;
   a connector in communication with said light detector and said light source, wherein said connector includes a plurality of terminals; and
   a booster circuit in communication with said light detector and wherein said booster circuit is disposed on said connector and is configured to reduce an input capacitance of at least one of said plurality of terminals.

* * * * *